United States Patent [19]

Ohkura

[11] Patent Number: 4,800,223
[45] Date of Patent: Jan. 24, 1989

[54] QUINOXALINONE DERIVATIVES AND ANALYTICAL METHOD USING SAID COMPOUNDS

[75] Inventor: Yosuke Ohkura, Fukuoka, Japan

[73] Assignee: Tosoh Corporation, Tokyo, Japan

[21] Appl. No.: 24,420

[22] Filed: Mar. 11, 1987

[30] Foreign Application Priority Data

Mar. 11, 1986 [JP] Japan ................... 61-51488

[51] Int. Cl.⁴ ............... C07D 241/44; G01N 33/52; G01N 30/02; G01N 21/64
[52] U.S. Cl. ................... 544/354; 436/131; 436/161; 436/172
[58] Field of Search ................... 544/354

[56] References Cited

U.S. PATENT DOCUMENTS 4,264,600 4/1981 Abdulla et al. ............. 544/354
4,296,114 10/1981 Appleton et al. ............ 544/354

OTHER PUBLICATIONS

Goto et al., Chem. Pharm. Bull., 29(3), 899-901 (1981).
Takadate et al., Chem. Pharm. Bull., 33(3), 1164-1169 (1985).
Goto et al., Anal. Chim. Acta, 147, 397-400 (1983).
Wintersteiger et al., J. Chromat., 237, 399-406 (1982).
Yamaguchi et al., J. Chromat., 346, 227-236 (1985).
Sen et al., Chemical Abstracts, vol. 55, 22329a (1961).

Primary Examiner—Mark L. Berch
Assistant Examiner—F. Bernhardt
Attorney, Agent, or Firm—Cushman, Darby & Cushman

[57] ABSTRACT

A quinoxalinone derivative of the following formula:

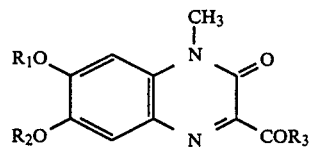

where $R_1$ and $R_2$ are each methyl, ethyl or propyl; and $R_3$ is a chlorine atom or azide, is a reagent capable of high-sensitivity labelling for fluorescence that reacts quantitatively with each of primary, secondary and tertiary hydroxyl groups to provide for easy labelling for fluorescence and which allows quantitative analyzing over a wide detection range.

2 Claims, 3 Drawing Sheets

1: PEAK DERIVED FROM DMEQ-COCl
2: PEAK DERIVED FROM DMEQ-COCl
3: DMEQ-COCl LABELED BENZYL ALCHOL
4: DMEQ-COCl LABELED CYCLOHEXANOL
5: DMEQ-COCl LABELED n-HEXANOL

6: PEAK WHOSE ORIGIN WAS UNKNOWN EXCEPT THAT IT DERIVED FROM DMEQ-CON$_3$
7: DMEQ-CON$_3$ LABELED BENZYL ALCOHOL
8: DMEQ-CON$_3$ LABELED CYCLOHEXANOL
9: DMEQ-CON$_3$ LABELED n-HEXANOL

10: PEAK DERIVED FROM DMEQ-CON$_3$
11: DMEQ-CON$_3$ LABELED VITAMIN D$_2$
12: DMEQ-CON$_3$ LABELED VITAMIN D$_3$

QUINOXALINONE DERIVATIVES AND ANALYTICAL METHOD USING SAID COMPOUNDS

BACKGROUND OF THE INVENTION

The present invention relates to a novel compound and a method of analyzing a hydroxy-containing compound with said novel compound being used as a labelling agent for fluorescence.

There are many compounds that contain a hydroxyl group. They exist in the human body in such forms as adrenocortical hormones, membrane components, bile acid, sex hormones, prostaglandins, and vitamins, and they are also available as natural and synthetic alcohols, medicines, perfumes, etc. Illustrative compounds that contain primary and secondary hydroxyl groups are corticosterone, and aldosterone; illustrative compounds that contain a secondary hydroxyl group are cholesterol, colic acid, $\beta$-estradiol, prostaglandin $E_2$ and ergocalciferol; compounds that contain secondary and tertiary hydroxyl groups include 2,5-hydroxycholecalciferol. Exemplary naturally occurring substances and synthetic medicines that contain a hydroxyl group include benzyl alcohol and lauryl alcohol which have a primary hydroxyl group; mephenesin having primary and secondary hydroxyl groups; cyclohexanol and propranolol which have a secondary hydroxyl group; and ecdysones having secondary and tertiary hydroxyl groups. Many of these compounds exhibit physiological activities in vivo in trace amounts, and some of the naturally occurring substances and synthetic medicines do so such as to produce toxicity. Analysis of these hydroxy-containing compounds will be useful not only in medical and biochemical studies but also in clinical and environmental testing applications. For this purpose, great benefit would be offered by a method that is capable of high-sensitivity analyzing of hydroxy-containing compounds in a sample of interest by labelling them for fluorescence. Many compounds have so far been proposed for use as reagents that can label the hydroxyl group for fluorescence, and they include: 4-dimethylamino-1-naphthoylnitrile (Chem. Pharm. Bull, 29 (3), 899–901 (1981)), 1-anthroylnitrile (Analytica Chimica. Acta, 147, 397–400 (1983)), 7-methoxycoumarin-3-carbonyl azide (Chem. Pharm. Bull, 33 (3), 1164–1169 (1985)), and naphthyl isocyanate (J. Chromatogr., 237, 399–406 (1982)).

These reagents are used in analyzing compounds having primary and secondary hydroxy groups in the following manner: a mixture of the reagent and a sample of interest is held at a temperature ranging from room temperature to 100° C. for a period of from 30 minutes to 2 hours until the sample is labelled for fluorescence, and the labelled sample is then subjected to high-performance liquid chromatography. The detection limits of these reagents are within the range of from 0.1 to 1 picomoles. The most sensitive 7-methoxycoumarin-3-carbonyl azide achieves a detection limit of 3 fentomoles for cholesterol; however, the intensity of fluorescence has a linear relationship with the amount of the sample in a very narrow range of 3 to 40 fentomoles and considerable skill is therefore required to achieve quantitative analyses. Naphthyl isocyanate has been used in analyzing steroid compounds having a tertiary hydroxyl group by performing reaction at 140° C. for a period of 120 minutes but the detection limit achieved is not very high and is within the range of 2.5 to 50 picomoles.

Under these circumstances, it has been desired to develop a reagent capable of high-sensitivity labelling for fluorescence that reacts quantitatively with each of primary, secondary and tertiary hydroxyl groups to provide for easy labelling for fluorescence and which ensures quantitative analyzing over a wide detection range.

SUMMARY OF THE INVENTION

An object, therefore, of the present invention is to provide a novel compound that satisfies the aforementioned requirements and which can be produced on an industrial scale.

Another object of the present invention is to provide a method of analyzing a hydroxy-containing compound by which a hydroxyl group can be labelled for fluorescence more readily than when the prior art reagents are used and which allows for higher-sensitivity analyzing.

DETAILED DESCRIPTION OF THE PREFERRED EMBODIMENT

Figure 1:
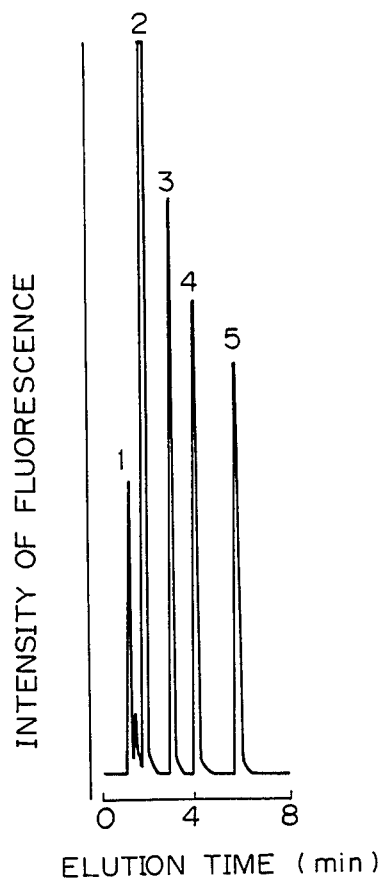
FIG. 1 is a chromatogram for primary and secondary alcohols that were labelled for fluorescence with DMEQ-COCl.

While the quinoxalinone derivatives of the present invention can be produced by a variety of methods, a typical process is hereinafter described.

Equal amounts of two known compounds, i.e., 4,5-dialkoxy-1,2-diaminobenzene and $\alpha$-ketomalonic acid, are reacted in a strong acid for several hours. Upon quenching, 3,4-dihydro-6,7-dialkoxy-3-oxo-quinoxaline-2-carboxylic acid is obtained. Illustrative alkoxys are those having 1–3 carbon atoms such as methoxy, ethoxy and propoxy. Illustrative strong acids are inorganic acids that are capable of achieving dehydration and condensation between the amino group in 4,5-dialkoxy-1,2-diaminobenzene and the carbonyl group in $\alpha$-ketomaloic acid. Specific examples of strong acids are hydrochloric acid, sulfuric acid and nitric acid, with hydrochloric acid being particularly preferable.

The resulting 3,4-dihydro-6,7-dialkoxy-3-oxo-quinoxaline-2-carboxylic acid is then subjected to methylation with diazomethane followed by ester hydrolysis with an alkali. The alkali may be an alkaline substance such as sodium hydroxide and potassium hydroxide that is capable of ester hydrolysis. The resulting aqueous solution is washed with a water-immiscible organic solvent several times and neutralized with an acid to form a precipitate. Usable organic solvents are those having intermediate polarity which will not mix with water. Specific examples of organic solvents include ethyl acetate, ether, chloroform and benzene, with ethyl acetate being preferable. Strong inorganic acids are used to neutralize the alkali and may be exemplified by hydrochloric acid and nitric acid, with hydrochloric acid being preferable. After precipitation, thionyl chloride is added to the reaction mixture, which is then boiled. Upon cooling, 3,4-dihydro-6,7-dialkoxy-4-methyl-3-oxo-quinoxaline- 2-carbonyl chloride (i.e., quinoxalinone derivative-carbonyl chloride) will result as a precipitate.

By reacting this quinoxalinone derivative-carbonyl chloride with sodium azide in an organic solvent, 3,4-dihydro-6,7-dialkoxy-4-methyl-3-oxo-quinoxalinone-2-carbony azide will form. The organic solvent is a non-polar solvent that dissolves the reactants so that they will be reacted rapidly. Illustrative organic solvents include acetone, benzene, toluene, etc. with acetone being particularly preferable.

The compounds obtained by the methods described above can be easily purified by routine procedures, that is, recrystallization and silica gel column chromatography. These compounds may be readily identified by routine analytical methods such as elemental analysis, mass spectrometry and infrared absorption spectroscopy.

Hydroxy-containing compounds may be labelled for fluorescence with the quinoxalinone derivatives of the present invention by carrying out a quantitative reaction between the two reactants at a temperature of at least 20° C., preferably between 50° and 100° C., for a period of at least 10 minutes, preferably between 30 minutes and one hour. The quinoxalinone derivative-carbonyl chloride reacts with a primary and secondary hydroxyl group to form a corresponding ester such that the latter is labelled for fluorescence. The quinoxalinone derivative-carbonyl azide reacts with a primary, secondary and tertiary hydroxyl group to form a corresponding carbamate such that the latter is labelled for fluorescence. If the reaction temperature is less than 20° C. or if the reaction time is less than 10 minutes, an undesirably slow reaction rate will result. The reaction rate is correlated with both reaction temperature and time in such a way that the higher the temperature, the more rapid is the progress of the reaction, and the longer the reaction time, the more thoroughly the reaction is performed. Therefore, in consideration of relevant factors such as the temperaturedependent stability of the sample, suitable reaction conditions may be selected from the temperature and time ranges specified above.

The organic solvent used in the reaction between the quinoxalinone derivatives and hydroxy-containing compounds may be selected from among aromatic hydrocarbons that dissolve the two reactants so that they will be reacted rapidly. Specific examples are benzene and toluene, with benzene being particularly preferable.

The following hydroxy-containing compounds may be labelled for fluorescence with the quinoxalinone derivatives of the present invention: substances that exist in the human body such as adrenocortical hormones (e.g. corticosterone and aldosterone), membrane building components (e.g. cholesterol), bile acid (e.g. colic acid), sex hormones (e.g. β-estradiol), prostaglandins (e.g. prostaglandin $E_2$), and vitamins (e.g. ergocalciferol, or vitamin $D_2$); natural and synthetic alcohols such as propanol, butanol, hexanol, lauryl alcohol, stearyl alcohol and cyclohexanol; medicines and perfumes such as benzyl alcohol and propranolol; natural insect ecdysis hormones such as ecdysones; and naturally occurring medicines such as digitalis (tertiary). The labelled compounds can be analyzed by liquid chromatography in accordance with routine procedures of high-performance liquid chromatography. For eluting ordinary reverse-phase packing materials, highly polar solvents such as water, methanol and acetonitrile may be used either singly or in admixture thereof. Depending upon the solubility of the labelled compounds, normal-phase packing materials may be used for elution with organic solvents of low polarity such as chloroform, ethanol and hexane.

According to the analytical method of the present invention, the intensity of fluorescence has a linear relationship with the amount of sample over a wide range of from 2 fentomoles to 2.5 picomoles, and the detection limit attained is within the range of 2–70 fentomoles.

- The following examples are provided for the purpose of further illustrating the present invention but are in no way to be taken as limiting.

EXAMPLE 1

Synthesis of 3,4-dihydro-6,7-dimethoxy-4-methyl-3-oxo-quinoxaline-2-carbonyl chloride (DMEQ-COCl) and 3,4-dihydro-6,7-dimethoxy-4-methyl-3-oxo-quinoxaline-2-carbonyl azide (DMEQ-CON$_3$)

The following reaction scheme was used:

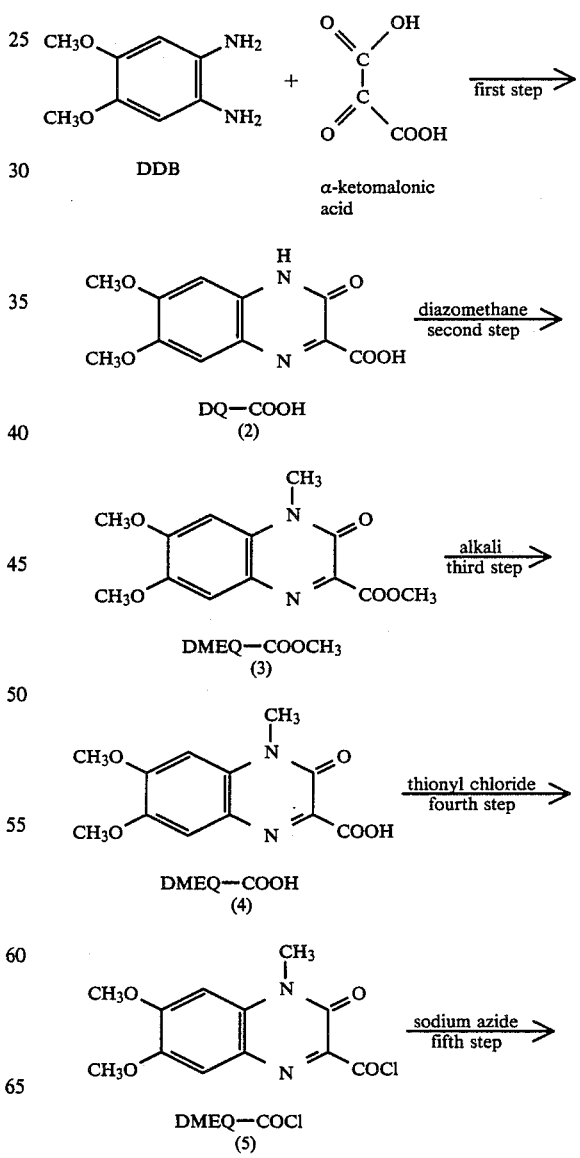

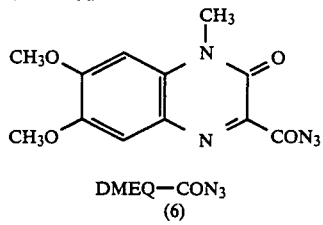

DMEQ—CON₃
(6)

The respective steps of this reaction scheme are described below in detail.

First Step

Eight grams of 1,2-diamino-4,5-dimethoxybenzene monohydrochloride (DDB) and an equal amount of α-ketomalonic acid were dissolved in 200 ml of 0.5N HCl. The mixture was boiled on a hot bath for 2 hours, then cooled. The resulting precipitate was washed with water and recrystallized from 90% dioxane, whereupon an orange needle of 3,4-dihydro-6,7-dimethoxy-3-oxo-quinoxaline-2-carboxylic acid (DQ-COOH) of formula (2) having a melting point of 268° C. was obtained in a yield of 55.9%.

Second Step

DQ-COOH (5.5 g) was dissolved in 50 ml of methanol, methylated with diazomethane and dried. The dried product was dissolved in 30 ml of chloroform and subjected to silica gel column chromatography, with a 1:1 mixture of n-hexane and ethyl acetate being used as an eluant. Upon concentration, dissolution and recrystallization, a yellow needle of methyl 3,4-dihydro-6,7-dimethoxy-4-methyl-3-oxo-quinoxaline-2-carboxylate (DMEQ-COOCH₃) of formula (3) having a melting point of 164° C. was obtained in a yield of 14.3% of DQ-COOH.

Third Step

DMEQ-COOCH₃ (2.5 g) was dissolved in 200 ml of 1.0 N sodium hydroxide and the solution was held at room temperature for 70 minutes to effect hydrolysis of DMEQ-COOCH₃. The resulting aqueous solution was washed with 200 ml of ethyl acetate five times and neutralized with HCl to produce a precipitate. Upon recrystallization from 80% 1,4-dioxane, a yellow needle of 3,4-dihydro-6,7-dimethoxy-4-methyl-3-oxo-quinoxaline-2-carboxylic acid (DMEQ-COOH) of formula (4) having a melting point of 222° C. was obtained in a yield of 78.6% of DMEQ-COOCH₃.

Fourth Step

DMEQ-COOH (1 g) and 20 ml of thionyl chloride were boiled for one hour. After cooling, 50 ml of petroleum ether was added to produce a precipitate. Upon recrystallization from a 9:1 mixture of benzene and petroleum ether, an orange needle of DMEQ-COCl of formula (5) having a melting point of 261° C. was obtained in a yield of 96.0% of DMEQ-COOH.

Fifth Step

DEMQ-COCl (1 g) was dissolved in 250 ml of acetone and the solution was subjected to reaction at 0° C. for 2 hours with sodium azide. The solution was then mixed with 200 ml of ice water to produce a precipitate. The precipitate was washed with water and recrystallized from benzene, whereupon an orange needle of DMEQ-CON₃ of formula (6) having a melting point of 271° C. was obtained in a yield of 85.0%.

The compounds obtained in steps 1 to 5 were subjected elemental analysis, infrared absorption spectroscopy and mass spectrometry, and the results are summarized in Table 1 below.

TABLE 1

| Compound | Elemental analysis (calculated values) | | | Mass spectrometry (M) | IR absorption | |
|---|---|---|---|---|---|---|
| | C | H | N | | C=O | C=C and/or C=N |
| DQ—COOH | 52.80 | 4.00 | 11.20 | 250 | 1730 | 1615 |
| | (52.71 | 4.02 | 11.13) | | 1635 | |
| DMEQ—COOCH₃ | 56.12 | 5.04 | 10.07 | 264 | 1735 | 1620 |
| | (56.13 | 5.04 | 9.98) | | 1640 | |
| DMEQ—COOH | 54.54 | 4.54 | 10.60 | 278 | 1740 | 1610 |
| | (54.51 | 4.52 | 10.58) | | 1635 | |
| DMEQ—COCl | 50.97 | 3.89 | 9.91 | 282.5 | 1750 | 1620 |
| | (50.94 | 3.77 | 9.81) | | 1645 | |
| DMEQ—CON₃ | 55.17 | 4.21 | 24.52 | 289 | 1700 | 1620 |
| | (55.2 | 4.18 | 24.49) | | 1645 | 2150 (N₃) |

(The parenthesized figures listed in the column of "Elemental analysis" are found values).

EXAMPLE 2

Labelling for fluorescence of primary and secondary alcohols with DMEQ-COCl and subsequent high-performance liquid chromatography on the labelled samples Five hundred microliters each of solutions containing 1.0 nanomoles/ml of benzyl alcohol, cyclohexanol and n-hexanol in benzene were mixed with 500 μl of a solution of 3 mM DMEQ-COCl in benzene and each of the mixtures was heated at 100° C. for 45 minutes to label the respective alcohols for fluorescence. Methanol (2 ml) was added to 20 μl of the reaction mixtures to prepare sample solutions and 10 μl of each sample was analyzed by high-performance liquid chromatography under the following conditions: column, reverse-phase column (YMC Pack C₈ of Yamamura Kagaku K. K.; 6 mm$^\phi$×15 cm$^L$); eluant, 70% methanol; and flow rate, 2.0 ml/min. Fluorescent detection was conducted with Hitachi F 1100 of Hitachi, Ltd. at $\lambda_{ex}$ of 400 nm and $\lambda_{em}$ of 500 nm. The chromatograph obtained is shown in FIG. 1, wherein the individual peaks correspond to 50 fentomoles.

The identity of the eluting position of each alcohol was verified by performing the above-described procedures on individual samples of alcohols.

EXAMPLE 3

Labelling for fluorescence of steroid compounds with DEMQ-COCl and subsequent high-performance liquid chromatography on the labelled samples Benzene solutions containing 1.0 nanomoles/ml of selected steroid compounds were subjected to labelling for fluorescence and high-performance liquid chromatography as in Example 2. The eluting positions and detection limits of the respective compounds are listed in Table 2 below. In order to ensure rapid elution, the compounds marked with an asterisk were eluted with methanol.

EXAMPLE 4

TABLE 2

| Compound | Elution time (min.) | Detection limit (fentomoles/10 μl) |
|---|---|---|
| 11-dehydrocorticosterone | 3.4 | 12.6 |
| deoxycorticosterone | 6.6 | 8.4 |
| pregnenolone | 28.8 | 15.2 |
| 17α-estradiol | 9.6 | 10.4 |
| dehydroisoandrosterone | 13.5 | 6.6 |
| cholesterol* | 4.9 | 4.6 |
| cholestanol* | 5.4 | 7.5 |

Figure 2:
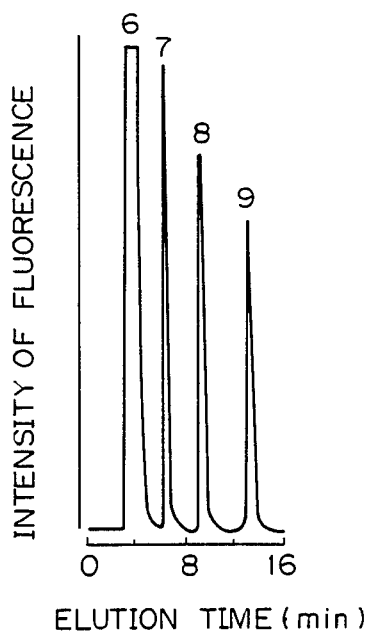
FIG. 2 is a chromatogram for primary and secondary alcohols that were labelled for fluorescence with DMEQ-CON$_3$.

Labelling for fluorescence of primary and secondary alcohols with DMEQ-CON$_3$ and subsequent high-performance liquid chromatography Ten microliters each of solutions containing 500 picomoles/ml of benzyl alcohol, cyclohexanol and n-hexanol in benzene were mixed with 100 μl of a solution of 2 mM DMEQ-CON$_3$ in benzene and the mixtures were heated at 100° C. for 45 minutes to label the respective alcohols for fluorescence. Methanol (1 ml) was added to the reaction mixtures to prepare sample solutions and 10 μl of each sample was analyzed by high-performance liquid chromatography under the same conditions as employed in Example 2 except that λ$_{ex}$ and λ$_{em}$ were 360 nm and 440 nm, respectively. The chromatogram obtained is shown in FIG. 2.

EXAMPLE 5

Labelling for fluroescence of steroid compounds with DMEQ-CON$_3$ and subsequent high-performance liquid chromatography Steriod compounds (50 nanomoles/ml) in benzene were labelled for fluorescence and subjected to high-performance liquid chromatography as in Example 4 except that 60% methanol was used as an eluant. The eluting time and detection limits of the respective compounds are listed in Table 3 below. In order to ensure rapid elution, the compounds marked with an asterisk were eluted with methanol.

TABLE 3

| Compound | Elution time (min.) | Detection limit (fentomoles/10 μl) |
|---|---|---|
| deoxycorticosterone | 7.4 | 5.76 |
| 11-dehydrocorticosterone | 3.7 | 5.95 |
| cortisone | 3.7 | 11.16 |
| corticosterone | 4.4 | 357.14 |
|  | 5.2 | 8.56 |
| pregnenolone | 40.6 | 12.50 |
| 17α-hydroxypregnenolone | 11.0 | 110.00 |
|  | 21.8 | 20.00 |
| dehydroisoandrosterone | 18.2 | 5.56 |
| 17α-estradiol | 9.6 | 312.50 |
|  | 11.4 | 69.40 |
|  | 12.2 | 625.00 |
| cholesterol* | 4.1 | 2.20 |

TABLE 3-continued

| Compound | Elution time (min.) | Detection limit (fentomoles/10 μl) |
|---|---|---|
| cholestanol* | 4.5 | 3.50 |

EXAMPLE 6

Labelling for fluorescence of tertiary alcohols with DMEQ-CON$_3$ and subsequent high-performance liquid chromatography Compounds (10 nanomoles/ml) having a tertiary hydroxyl group were dissolved in benzene and subjected to labelling for fluorescence and high-performance liquid chromatography as in Example 5. The eluting time and detection limits of the respective compounds are listed in Table 4 below.

TABLE 4

| Compound | Elution time (min.) | Detection limit (fentomoles/10 μl) |
|---|---|---|
| 2-methyl-2-propanol | 6.80 | 19.7 |
| 2-methyl-2-butanol | 4.75 | 5.7 |
| 2-methyl-2-pentanol | 7.90 | 6.9 |
| ethisterone | 11.50 | 44.6 |

EXAMPLE 7

Figure 3:
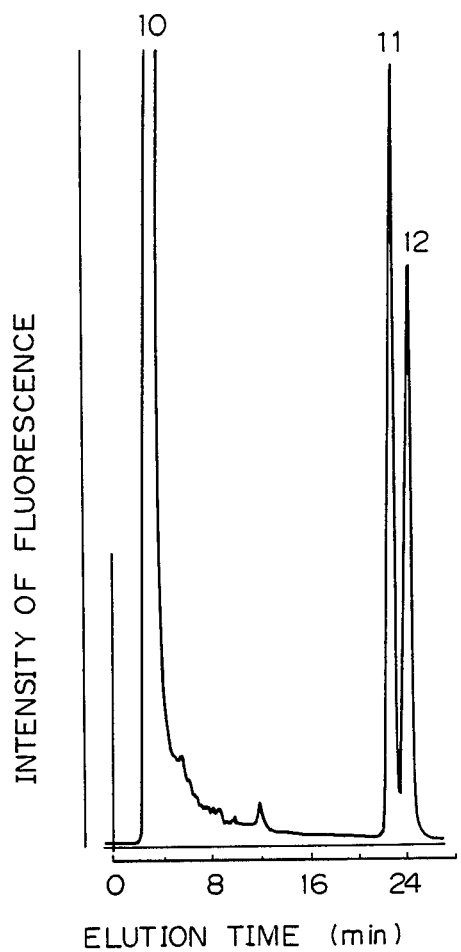
FIG. 3 is a chromatogram for vitamins D$_2$ and D$_3$ that were labelled for fluorescence with DMEQ-CON$_3$.

Labelling for fluorescence of vitamins D$_2$ and D$_3$ with DEMQ-CON$_3$ and subsequent high-performance liquid chromatography Benzene solutions (20 μl) containing 10 nanomoles/ml of vitamins D$_2$ and D$_3$ were mixed with 100 μl of a benzene solution containing 1.0 mM DMEQ-CON$_3$ and the respective mixtures were heated at 50° C. for 60 minutes to label the vitamins for fluorescence. To the reaction mixtures, 1 ml of methanol was added to prepare sample solutions, and 10 μl of each sample was analyzed by high-performance liquid chromatography under the following conditions: column, reverse-phase column (TSK Gel ODS-120T of Toyo Soda Manufacturing Co., Ltd.; 4.6 mm$^\phi$×25 cm$^L$); eluant, 98% methanol; and flow rate, 1.0 ml/min. Fluorescent detection was conducted at λ$_{ex}$ 360 nm and λ$_{em}$ 440 nm. The chromatogram obtained is shown in FIG. 3.

The advantages of the present invention are summarized below:

(1) It offers a reagent that can be conveniently used to label primary, secondary or tertiary hydroxyl group for fluorescence. It is most characteristic that a tertiary hydroxyl group can be labelled for fluorescence as conveniently as primary and secondary hydroxyl groups.

(2) It allows for high-sensitivity analysis with the detection limit being improved to a value of 2–70 fentomoles.

(3) The intensity of fluorescence has a linear relationship with the dose of sample over a wide range of from 2 fentomoles to 2.5 picomoles and this allows labelling for fluorescence and high-sensitivity analysis to be achieved without requiring great skill on the part of the operator.

What is claimed is:

1. A compound of the following formula:

where R$_1$ and R$_2$ are each methyl, ethyl or propyl; and R$_3$ is a chlorine atom or azide.

2. The compound according to claim 1 wherein R$_1$ and R$_2$ are each methyl.

* * * * *